(12) United States Patent
Heo et al.

(10) Patent No.: US 8,900,660 B2
(45) Date of Patent: Dec. 2, 2014

(54) SILVER COATING PIGMENT, AND METHOD FOR PRODUCING SAME

(75) Inventors: Dong-Min Heo, Pyeongtaek-si (KR); Jae-Il Jeong, Cheongju-si (KR); Kwang-Choong Kang, Cheongju-si (KR); Byung-Ki Choi, Chungcheongbuk-do (KR); Kwang-Soo Lim, Cheongju-si (KR); Kil-Wan Chang, Cheongju-si (KR); Man-Su Lee, Cheongju-si (KR); Gun-Eik Jang, Cheongju-si (KR)

(73) Assignee: CQV Co., Ltd., Jincheon-Gun, Chungcheongbuk-Do ( * ) Notice: Subject to any disclaimer, the term of this patent is extended or adjusted under 35 U.S.C. 154(b) by 0 days.

(21) Appl. No.: 14/113,299

(22) PCT Filed: Apr. 12, 2012

(86) PCT No.: PCT/KR2012/002765
§ 371 (c)(1),
(2), (4) Date: Oct. 22, 2013

(87) PCT Pub. No.: WO2012/148104
PCT Pub. Date: Nov. 1, 2012

(65) Prior Publication Data
US 2014/0050769 A1    Feb. 20, 2014

(30) Foreign Application Priority Data
Apr. 28, 2011    (KR) .................. 10-2011-0039975

(51) Int. Cl.
| | | |
|---|---|---|
| C09C 1/62 | (2006.01) | |
| C09C 3/00 | (2006.01) | |
| C09C 3/06 | (2006.01) | |
| C09C 3/08 | (2006.01) | |
| C23C 18/16 | (2006.01) | |
| C23C 18/42 | (2006.01) | |
| C23C 18/44 | (2006.01) | |
| C09C 1/00 | (2006.01) | |
| C09C 1/40 | (2006.01) | |
| C09C 1/24 | (2006.01) | |
| C09C 1/30 | (2006.01) | |
| C23C 18/18 | (2006.01) | |

(52) U.S. Cl.
CPC ................ *C09C 1/0078* (2013.01); *C09C 1/405* (2013.01); *C09C 1/407* (2013.01); *C09C 1/24* (2013.01); *C09C 1/30* (2013.01); *C23C 18/1635* (2013.01); *C23C 18/1893* (2013.01); *C23C 18/44* (2013.01); *C01P 2004/20* (2013.01); *C01P 2006/62* (2013.01); *C01P 2006/63* (2013.01); *C01P 2006/64* (2013.01)
USPC ........... 427/217; 106/403; 106/415; 106/417; 427/218; 427/310; 427/404

(58) Field of Classification Search
USPC .......... 106/403, 415, 417; 427/217, 218, 310, 427/404
See application file for complete search history.

(56) References Cited

U.S. PATENT DOCUMENTS

| | | | |
|---|---|---|---|
| 7,544,415 B2 | 6/2009 | Chen et al. | |
| 2004/0237844 A1* | 12/2004 | Pfaff et al. | .................... 106/415 |
| 2011/0126735 A1 | 6/2011 | Yu et al. | |

FOREIGN PATENT DOCUMENTS

| | | |
|---|---|---|
| CN | 1575322 A | 2/2005 |
| EP | 1707599 A1 | 10/2006 |
| EP | 2147954 A1 | 1/2010 |
| EP | 2333019 A1 | 6/2011 |
| KR | 1020070013982 A | 1/2007 |
| KR | 1020100016281 A | 2/2010 |

OTHER PUBLICATIONS

International Search Report for PCT/KR2012/002765 mailed Nov. 22, 2012, citing the above reference(s).
Extended European Search Report dated Sep. 1, 2014.

* cited by examiner

*Primary Examiner* — Anthony J Green
(74) *Attorney, Agent, or Firm* — Lowe Hauptman & Ham, LLP

(57) ABSTRACT

Disclosed is a method for producing a silver (Ag) coating pigment. The method for producing a silver coating pigment according to the present invention comprises: a step of forming a tin compound pretreatment layer on the matrix surface; and a step of forming a silver coating layer on the lower portion of the tin compound pretreatment layer through a reflux and electroless plating process using a diluted solution of silver nitrate, ammonia water, a citric acid solution, and a diluted solution of potassium hydroxide.

11 Claims, 1 Drawing Sheet

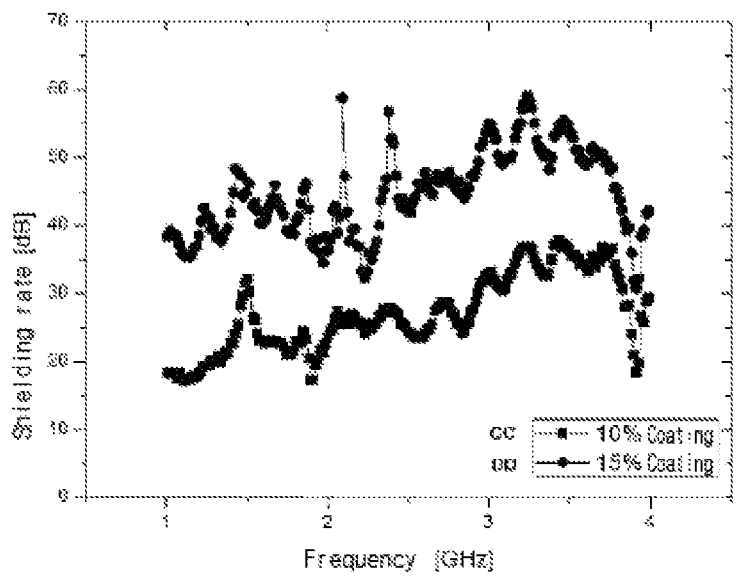

SILVER COATING PIGMENT, AND METHOD FOR PRODUCING SAME

CROSS REFERENCE TO RELATED APPLICATION

This application claims the priority of Korean Patent Application No. 10-2011-0039975, filed on Apr. 28, 2011 in the Korean Patent and Trade Mark Office. Further, this application is the National Phase application of International Application No. PCT/KR2012/002765 filed on Apr. 12, 2012, which is incorporated herein by reference in its entirety.

TECHNICAL FIELD

The present invention relates to a silver-coated pigment and a method for preparing the same, and more particularly, to a technique capable of easily producing a high brightness silver-coated pigment having improved economic feasibility by improving coating efficiency of electroless plating without using expensive compounds such as $PdCl_2$ as a pre-treatment material.

BACKGROUND ART

Pearlescent pigments are formed using powders, which have a coating layer formed on a transparent matrix of the powder. Here, typically, high refractive index metal oxides such as $TiO_2$, $Fe_2O_3$ and the like and low refractive index materials such as $SiO_2$, $MgO.SiO_2$ are used to coat the transparent matrix. Such materials are coated onto the transparent matrix as a single layer or multiple layers, thereby preparing pearlescent pigments of various colors.

However, the pearlescent pigments have problems in that it is not easy to perform a process for preparing an initial reaction solution using a metal salt, which is a starting material in a process for preparing metal oxides, and in that the pigments do not have high gloss unlike metals due to optical properties of the metal oxides.

DISCLOSURE

Technical Problem

An aspect of the present invention is to provide a method for preparing a silver-coated pigment, which has improved efficiency and can reduce production costs by eliminating expensive metal compounds such as $PdCl_2$ in formation of a pre-treatment layer and expensive devices, such as sputters, microwave irradiators and the like, in a silver coating process in the preparation of a pigment having a stacked structure of a pre-treatment layer and a silver (Ag) coating layer.

Another aspect of the present invention is to provide a method for preparing a silver-coated pigment, which can reduce costs for processes and facilities by integrating and simplifying conventional cleaning, sensitization and activation processes into a single refluxing process in formation of a silver (Ag) coating layer.

Technical Solution

In accordance with one embodiment of the present invention, a method for preparing a silver (Ag)-coated pigment includes: forming a tin compound pre-treatment layer on a matrix surface; and forming a silver coating layer on the tin compound pre-treatment layer through refluxing and electroless plating using a silver nitrate diluted solution, aqueous ammonia, a citric acid solution, and a dilute dilute potassium hydroxidesolution.

More specifically, the method for preparing a silver (Ag) coating pigment includes: (a) preparing a slurry by mixing a matrix with a hydrochloric acid solution; (b) removing impurities from the surface of the matrix by refluxing the slurry; (c) forming a $SnCl_2$ pre-treatment layer on the surface of the matrix by adding $SnCl_2.2H_2O$ to the slurry of (b) and refluxing the slurry; (d) forming a pigment powder coated with the $SnCl_2$ pre-treatment layer through dehydration and water-washing of the slurry; (e) forming a dilute silver nitrate solution by mixing silver nitrate, pure water, aqueous ammonia and sodium citrate, and forming a suspension by mixing the pigment powder coated with the $SnCl_2$ pre-treatment layer with the dilute silver nitrate solution; (f) mixing the suspension with a dilute glucose solution and refluxing the mixture; (g) mixing the suspension of (f) with a dilute potassium hydroxide (KOH) solution and additionally refluxing the mixture; (h) adding a citric acid solution to the suspension of (g), and forming a silver (Ag) coating layer on the pre-treatment layer by refluxing and electroless plating; and (i) performing dehydration and water-washing of the suspension of (h), and drying the resulting suspension.

Advantageous Effects

According to the invention, the method for preparing a silver (Ag)-coated pigment may reduce production costs and investment costs for facilities by forming a pre-treatment layer without using expensive metal compounds such as $PdCl_2$.

In addition, the method for preparing a silver (Ag)-coated pigment may reduce process costs and improve production efficiency by integrating and simplifying conventional processes into a single reflux process without use of an conventional sputtering or microwave irradiation process.

Further, according to the invention, the silver (Ag)-coated pigment has excellent antibacterial properties and electromagnetic wave shielding effects.

BRIEF DESCRIPTION OF DRAWINGS

FIG. 1 is a graph depicting electromagnetic wave shielding effects of pigment powders according to embodiments of the present invention.

BEST MODE

The above and other aspects, features and advantages of the present invention will become apparent from the detailed description of the following embodiments in conjunction with the accompanying drawings. However, it should be understood that the present invention is not limited to the following embodiments and may be embodied in different ways, and that the embodiments are provided for complete disclosure and thorough understanding of the invention by those skilled in the art. The scope of the invention should be limited only by the accompanying claims and equivalents thereof.

Hereinafter, a silver (Ag)-coated pigment and a method for preparing the same according to embodiments of the invention will be described in detail.

According to one embodiment of the invention, a pigment includes: a pre-treatment layer formed on a matrix surface to facilitate coating; and a silver coating layer formed on the pre-treatment layer.

An conventional pre-treatment process has low economic feasibility since the pre-treatment process is performed using expensive compounds such as $PdCl_2$ or through several processes. However, if pre-treatment is not performed, there is a problem in that a sputtering device or a microwave irradiator is used for silver coating, thereby increasing equipment costs.

Thus, according to the invention, a slurry is prepared using hydrochloric acid (HCl) and a tin compound ($SnCl_2.2H_2O$), followed by refluxing, thereby forming a pre-treatment layer of the tin compound on the matrix.

Pre-Treatment

First, a slurry containing a solid content of 10% by weight (wt %) to 20 wt % is prepared using a matrix, preferably a flake which is a flat matrix, and a hydrochloric acid solution diluted to a concentration of 1 wt % to 10 wt %.

Here, the matrix includes at least one selected from among glass flakes, mica, titania-coated glass flakes, titania-coated mica, iron oxide-coated mica, iron oxide-coated glass flakes, plate-shaped iron oxide, plate-shaped alumina, and plate-shaped silica.

In addition, if the hydrochloric acid solution has a concentration of less than 1 wt %, subsequent removal of impurities can be difficult, and if the hydrochloric acid solution has a concentration of greater than 10 wt %, a subsequent process for forming a coating layer can be abnormally performed due to excessive etching of the matrix surface.

Further, if the slurry has a solid content of less than 10 wt % in the slurry, productivity can be decreased due to insufficient amount of the matrix, and if the slurry has a solid content of greater than 20 wt %, time required to form the coating layer is increased, deteriorating process efficiency.

After preparation of the slurry, the slurry is refluxed for 1 hour to 3 hours, such that all of impurities can be removed from the surface of the matrix.

Thus, if refluxing time is less than 1 hour, the impurities can be insufficiently removed, and if the refluxing time exceeds 3 hours, the surface of the matrix can be excessively etched, whereby a subsequent coating process can be abnormally performed.

After completion of pre-treatment of the surface of the matrix, a tin compound such as $SnCl_2.2H_2O$ is added to the slurry, followed by refluxing for 1 hour to 3 hours, thereby forming a tin compound pre-treatment layer, such as 1 part by weight to 10 parts by weight of $SnCl_2$ based on 100 parts by weight of the matrix, on the surface of the matrix.

Here, if the tin compound pre-treatment layer is formed in an amount of less than 1 part by weight based on 100 parts by weight of the matrix, the tin compound pre-treatment layer has an extremely small thickness and thus insufficiently functions as the pre-treatment layer. Conversely, if the tin compound pre-treatment layer is formed in an amount of greater than 10 parts by weight based on 100 parts by weight of the matrix, cracking can occur in the subsequent coating process due to increased thickness, and properties of the pigment, such as gloss and brightness, can be deteriorated.

In addition, if the refluxing time is less than 1 hour, the tin compound pre-treatment layer can be insufficiently formed in an amount of less than 1 part by weight based on 100 parts by weight of the matrix. Further, if the refluxing time exceeds 3 hours, the tin compound pre-treatment layer is formed in an amount of greater than 10 parts by weight based on 100 parts by weight of the matrix, thereby causing an excessively large thickness of the pre-treatment layer.

After completion of the pre-treatment process as described above, the slurry is dehydrated and washed with pure water, thereby completing the preparation of the pigment powder coated with the pre-treatment layer.

Next, in order to secure high brightness for the pigment according to the invention, a silver coating layer is formed on the surface of the pigment powder.

Here, for silver coating, the following three types of solutions are prepared. Next, the pre-treated pigment powder is added to a suspension in which the prepared solutions are mixed, followed by refluxing, thereby performing silver coating.

As such, the silver coating process according to the invention can simplify the preparation process by elimination of an conventional plating process, and can improve economic feasibility as $PdCl_2$, which is extremely costly, is not used.

Silver Coating

1) Dilute Silver Nitrate Solution

A dilute silver nitrate solution is prepared by adding pure water, aqueous ammonia and sodium citrate to 10 parts by weight to 70 parts by weight of silver nitrate based on 100 parts by weight of the matrix.

Here, the amount of silver nitrate may vary according to the particle size of the matrix. If the matrix has a large particle size, an added amount of the silver nitrate can be decreased to 10 parts by weight based on 100 parts by weight of the matrix, and if the matrix has a small particle size, an added amount of the silver nitrate can be increased to 70 parts by weight based on 100 parts by weight of the matrix.

However, if the amount of silver nitrate is less than 10 parts by weight based on 100 parts by weight of the matrix, effects of silver coating can become insignificant, and if the amount of silver nitrate exceeds 70 parts by weight based on 100 parts by weight of the matrix, the silver coating layer has an excessively large thickness, thereby causing problems in terms of economic feasibility.

Next, the aqueous ammonia is preferably present in an amount of 50 parts by weight to 150 parts by weight based on 100 parts by weight of silver nitrate.

If the added amount of the aqueous ammonia is less than 50 parts by weight based on 100 parts by weight of silver nitrate, silver can be partially oxidized, such that the dilute silver solution has a non-transparent color, that is, a translucent or opaque color. As a result, in formation of the coating layer, crystal growth and adhesion can be deteriorated. Conversely, if the added amount of the aqueous ammonia exceeds 150 parts by weight based on 100 parts by weight of silver nitrate, reaction efficiency can be decreased due to deterioration in capabilities of reduction into silver, and facility conditions can be harmed due to the foul odor of the aqueous ammonia.

Next, based on 100 parts by weight of silver nitrate, 15 parts by weight to 100 parts by weight of sodium citrate is added to the dilute silver nitrate solution, followed by refluxing.

Here, if the amount of sodium citrate is less than 15 parts by weight based on 100 parts by weight of silver nitrate, adhesion of the silver coating layer can be decreased, thereby making it difficult to form dense crystals. Conversely, if the amount of sodium citrate exceeds 100 parts by weight based on 100 parts by weight of silver nitrate, agglomeration of the silver-coated particles may occur due to increased cation concentration.

2) Dilute Glucose Solution

Based on 100 parts by weight of silver nitrate, 100 parts by weight to 200 parts by weight of glucose is diluted with pure water. The dilute glucose solution may contain about 5 wt % to about 30 wt % of glucose, without being limited thereto.

Here, if the added amount of glucose is less than 100 parts by weight, economic feasibility can be deteriorated due to the presence of silver ions in the solution after completion of reaction. If the added amount of glucose exceeds 200 parts by weight, the effects of glucose addition may no be exhibited.

3) Dilute Potassium Hydroxide Solution

Based on 100 parts by weight of silver nitrate, 100 parts by weight to 200 parts by weight of potassium hydroxide is diluted with pure water. The dilute potassium hydroxide solution may contain about 5 parts by weight to about 30 parts by weight of potassium hydroxide, without being limited thereto.

Here, the dilute potassium hydroxide solution preferably contains 100 parts by weight to 200 parts by weight of potassium hydroxide based on 100 parts by weight of silver nitrate. If the amount of potassium hydroxide is less than 100 parts by weight based on 100 parts by weight of silver nitrate, adhesion of the silver coating layer can be deteriorated, thereby inhibiting the formation of dense crystals. Conversely, if the amount of potassium hydroxide exceeds 200 parts by weight based on 100 parts by weight of silver nitrate, agglomeration of the silver-coated particles may occur, causing non-uniform coating.

As described above, after completion of preparation of major solutions for silver coating, a suspension is prepared by adding the pre-treated pigment powder to the dilute silver nitrate solution. Next, the dilute glucose solution is added to the suspension, which in turn is immediately refluxed.

Next, the dilute potassium hydroxide solution is slowly added to the suspension over a period of 30 minutes to 3 hours using a metering pump.

Here, if the dilute potassium hydroxide solution is added for an insufficient time of less than 30 minutes, crystal growth for subsequent silver coating can be deteriorated, and refluxing can be insufficiently performed. Conversely, if the adding time of the dilute potassium hydroxide solution exceeds 30 minutes, silver is transformed from silver nitrate into silver oxide, causing abnormal performance of the coating process, and economic feasibility can be deteriorated due to increase in preparation time.

As described above, after adding the dilute potassium hydroxide solution to the suspension, the resulting suspension is additionally refluxed for about 30 minutes to about 3 hours.

Next, based on 100 parts by weight of silver nitrate, 50 parts by weight to 200 parts by weight of a citric acid solution is added to the suspension after completion of the additional reflux process, and refluxing for 50 minutes to 70 minutes and electroless plating are finally performed, thereby preparing a pigment, on which 10 parts by weight to 35 parts by weight of the silver coating layer is formed based on 100 parts by weight of the matrix.

Here, if the added amount of the citric acid solution is less than 50 parts by weight based on 100 parts by weight of silver nitrate, or the refluxing time is less than 50 minutes, dispersibility of partially agglomerated particles inside the solution can be deteriorated. Conversely, if the added amount of the citric acid solution exceeds 200 parts by weight based on 100 parts by weight of silver nitrate, or the refluxing time exceeds 70 minutes, the coated silver may re-dissolve into the aqueous solution.

Next, after the resulting suspension is dehydrated and washed with pure water, the suspension is dried at 30° C. to 100° C., thereby preparing a pigment powder on which the silver coating layer is formed. Here, if the drying temperature is less than 30° C., economic feasibility can be deteriorated due to excessively long drying time, and if the drying temperature exceeds 100° C., there can be a possibility of damage to silver-coated particles having an enlarged specific surface area, and agglomeration of the silver-coated particles can be increased.

As such, the pigment powder having the silver coating layer according to the invention can be easily prepared, and has high brightness and improved economic feasibility through elimination of expensive compounds such as $PdCl_2$ as a pre-treatment material and electroless plating with low coating efficiency.

Thus, the pigment powder has improved brightness due to the high brightness of the added metal, silver (Ag).

In addition, antibacterial properties of silver can be improved, and a specific surface area of silver is increased by a coating method using the suspension, such that the pigment can have improved brightness and antibacterial properties in proportion to increase in the specific surface area of the silver. That is, the pigment may have higher properties in terms of brightness, gloss and chroma than coated pigments produced by conventional electroless plating methods. Next, the present invention will be explained in more detail with reference to some examples.

Measurement Results

Table 1 shows colorimeter measurement values depending on parts by weight of a silver coating layer and sodium citrate based on 100 parts by weight of a matrix. The matrix was composed of glass flakes, and 5 parts by weight of a $SnCl_2$ pre-treatment layer was formed based on 100 parts by weight of the matrix before formation of the silver coating layer.

Measurement of samples of Examples and Comparative Examples was performed on a black background after draw-down of the samples to PC 6% (with NC Resin) on an opacity chart.

1) Colorimeter Measurement Values (Measured Using a MINOLTA Cm-512 m3 at 75 Degrees)

TABLE 1

|  | Matrix (parts by weight) | Silver coating layer (parts by weight) | Sodium citrate (parts by weight) | L | a | b |
| --- | --- | --- | --- | --- | --- | --- |
| Comparative Example 1 | 100 | 5 | 4 | 18.81 | −3.28 | 4.35 |
| Example 1 | 100 | 10 | 4 | 21.83 | −2.36 | 2.24 |
| Example 2 | 100 | 15 | 4 | 22.48 | −2.18 | 2.55 |
| Example 3 | 100 | 15 | 8 | 21.81 | −1.44 | 3.04 |
| Example 4 | 100 | 25 | 4 | 22.29 | −2.02 | 0.96 |
| Example 5 | 100 | 25 | 8 | 23.55 | −1.93 | 1.02 |
| Example 6 | 100 | 35 | 8 | 23.78 | −1.39 | 1.82 |
| Comparative Example 2 | 100 | 40 | 4 | 24.89 | −0.99 | 1.54 |

Referring to Table 1, it can be seen that all of the samples of Examples 1 to 6 have higher luminosity (L) values than those of Comparative Examples 1 to 2. In addition, it can be seen that while a and b values of Examples 1 to 6 are distributed in a region close to colorlessness, a and b values of Comparative Examples 1 to 2 are weighted towards a colored region. Thus, it can be seen that the silver coating layer according to the invention had improved brightness and chroma.

2) Gloss Meter Measurement Value (Measured Using a DENSHOKU PG-1M at 60 Degrees)

TABLE 2

|  | Comparative Example 1 | Example 1 | Example 2 | Example 3 | Example 4 | Example 5 | Example 6 | Comparative Example 2 |
|---|---|---|---|---|---|---|---|---|
| Gloss | 101.6 | 134.9 | 134.6 | 133.9 | 118.9 | 107.8 | 106.5 | 105.2 |

Referring to Table 2, it can be seen that all of the samples of Examples 1 to 6 have superior gloss properties to Comparative Examples 1 to 2.

According to the invention, the silver (Ag)-coated pigment provides excellent antibacterial properties and electromagnetic wave shielding effects in addition to excellent gloss properties.

Next, antibacterial properties of the pigment powder according to the invention will be described in more detail based on test results.

Testing was outsourced to the FITI Testing & Research Institute, and antimicrobial activity testing was performed in accordance with the KS 4206:2008, SHAKE FLASK METHOD.

The pigments prepared in Examples 1 and 2 were used as samples, and the pigments prepared in Comparative Examples 3 and 4 were used as samples, in which only the silver coating layer was excluded from the pigments of Examples 1 and 2.

With the same amount of bacteria placed in each sample, test results were measured after 24 hours. Results are shown in Table 3.

TABLE 3

|  | Comparative Example 3 | Example 1 | Comparative Example 4 | Example 2 |
|---|---|---|---|---|
| Initial moment | $1.7 * 10^4$ | $1.7 * 10^4$ | $1.5 * 10^4$ | $1.5 * 10^4$ |
| After 24 hours | $9.3 * 10^6$ | <10 | $1.3 * 10^5$ | <10 |
| Removal rate (%) | — | 99.9 | — | 99.9 |

From Table 3, it can be seen that the samples of Examples 1 and 2 had much higher bacteria removal rates than those of Comparative Examples 3 and 4.

Next, in order to investigate electromagnetic wave shield effects of the pigment powder according to the invention, electromagnetic wave shield testing was performed using the pigments of Examples 1 and 2.

Testing was performed by the Chungbuk TechnoPark IT Convergence Center (Korea) in accordance with Article 23 of the Framework Act on international standards, Enforcement decree Article 16, and KS A ISO/IEC 17025:2006.

In addition, results are shown in Table 4, and a graph is shown in FIG. 1. In FIG. 1, 10% coating means that the silver coating layer is present in an amount of 10 parts by weight based on 100 parts by weight of the matrix, and 15% coating means that the silver coating layer is present in an amount of 15 parts by weight based on 100 parts by weight of the matrix.

TABLE 4

| Frequency | Shielding rate (dB) | |
|---|---|---|
| (GHz) | Example 1 | Example 2 |
| 1.012 | 18.31 | 38.39 |
| 1.102 | 17.33 | 35.76 |

TABLE 4-continued

| Frequency | Shielding rate (dB) | |
|---|---|---|
| (GHz) | Example 1 | Example 2 |
| 1.207 | 18.05 | 38.47 |
| 1.313 | 19.97 | 38.15 |
| 1.403 | 22.57 | 41.77 |
| 1.508 | 32.00 | 46.29 |
| 1.599 | 22.95 | 40.29 |
| 1.704 | 22.50 | 42.95 |
| 1.809 | 22.83 | 40.61 |
| 1.900 | 17.29 | 37.57 |
| 2.005 | 23.38 | 36.29 |
| 2.110 | 25.78 | 47.25 |
| 2.201 | 25.77 | 36.93 |
| 2.306 | 25.55 | 37.63 |
| 2.396 | 27.80 | 52.70 |
| 2.502 | 24.30 | 41.99 |
| 2.607 | 24.11 | 47.77 |
| 2.697 | 27.99 | 46.20 |
| 2.803 | 25.66 | 45.09 |
| 2.908 | 27.64 | 47.05 |
| 2.998 | 32.64 | 54.93 |
| 3.104 | 30.72 | 49.50 |
| 3.209 | 36.75 | 57.04 |
| 3.299 | 34.13 | 52.54 |
| 3.314 | 33.69 | 51.50 |
| 3.329 | 33.20 | 50.49 |
| 3.344 | 32.61 | 50.14 |
| 3.360 | 32.43 | 50.59 |
| 3.375 | 32.97 | 48.23 |
| 3.390 | 35.01 | 49.92 |
| 3.405 | 37.05 | 53.14 |
| 3.495 | 36.51 | 54.59 |
| 3.600 | 34.37 | 48.82 |
| 3.706 | 36.82 | 50.55 |
| 3.796 | 32.88 | 45.24 |
| 3.901 | 20.91 | 31.81 |
| 3.992 | 29.36 | 42.09 |

From Table 4 and FIG. 1, it can be seen that all of the pigment powders according to the invention had an electromagnetic wave shielding rate of 10 dB or more. From this result, it can be seen that the pigment powder according to the invention has excellent electromagnetic wave shielding efficiency.

As described above, according to the invention, the method for preparing a sliver (Ag)-coated pigment can reduce production costs and investment costs for facilities by elimination of expensive metal compounds such as $PdCl_2$ and expensive devices, such as a sputtering device, a microwave irradiator, and the like, upon formation of the pre-treatment layer.

In addition, the method for preparing a silver (Ag)-coated pigment can reduce process costs and improve production efficiency by integrating and simplifying conventional processes into a single reflux process without using conventional electroless plating.

According to the invention, the silver-coated pigment can be used as a pigment for cosmetics, such as lipsticks, eye shadows, nail polishes, and the like.

Tables 5 to 7 show compositions of lipsticks (Table 5), eye shadows (Table 6), and nail polishes (Table 7) including the pigment prepared in Example 2 and MC2080PS (Nippon sheet glass Co., Ltd.).

Table 5 shows compositions of Lipstick 1 employing the pigment prepared in Example 2 and Lipstick 2 employing a pigment MC2080PS.

TABLE 5

(unit: wt %)

| Component | Lipstick 1 | Lipstick 2 |
|---|---|---|
| Pigment | 10.0 | 10.0 |
| Hydrogenated Castor Oil | 32.75 | 32.75 |
| Octyldodecanol | 9.00 | 9.00 |
| Diisostearyl Malate | 9.00 | 9.00 |
| Microcrystalline wax | 7.20 | 7.20 |
| Ceresin | 4.50 | 4.50 |
| *Euphorbia Cerifera* (Candelilla) wax | 4.50 | 4.50 |
| Dipentaerythrityl Hexahydroxy stearate/Hexastearate/Hexarosinate | 4.50 | 4.50 |
| *Simmondsia Chinensis* (Jojoba) Seed Oil | 4.50 | 4.50 |
| Isopropyl Myristate | 4.50 | 4.50 |
| Mineral Oil | 3.15 | 3.15 |
| *Copernicia Cerifera* (Carnauba) wax | 2.70 | 2.70 |
| Isopropyl Lanolate | 1.80 | 1.80 |
| VP/Hexadecene Copolymer | 0.90 | 0.90 |
| Tocopheryl Acetate | 0.45 | 0.45 |
| Bees wax | 0.27 | 0.27 |
| Sorbitan SesQuioleate | 0.18 | 0.18 |
| Propylparaben | 0.09 | 0.09 |
| BHT | 0.01 | 0.01 |
| Total | 100.00 | 100.00 |

Table 6 shows compositions of Eye shadow 1 employing the pigment prepared in Example 2 and Eye shadow 2 employing a pigment MC2080PS.

TABLE 6

(unit: wt %)

| Component | Eye shadow 1 | Eye shadow 2 |
|---|---|---|
| Pigment | 10.0 | 10.0 |
| Talc | 68.40 | 68.40 |
| Mica | 7.20 | 7.20 |
| Zinc Stearate | 5.40 | 5.40 |
| Silica | 4.50 | 4.50 |
| Methyl Methacrylate crosspolymer | 2.88 | 2.88 |
| Titanium dioxide | 1.44 | 1.44 |
| Aluminum Myristate | 0.09 | 0.09 |
| Triethoxy caprylyl silane | 0.05 | 0.05 |
| Dimethicone | 0.04 | 0.04 |
| Total | 100.00 | 100.00 |

Table 7 shows compositions of Nail polish 1 employing the pigment prepared in Example 2 and Nail polish 2 employing a pigment MC2080PS.

TABLE 7

(unit: wt %)

| Component | Nail polish 1 | Nail polish 2 |
|---|---|---|
| Pigment | 3.00 | 3.00 |
| Nitrocellulose (1/2 seconds) | 10.00 | 10.00 |
| Alkyd resin | 10.00 | 10.00 |
| Acetyl Tributyl Citrate | 2.00 | 2.00 |
| Ethyl Acetate | 20.00 | 20.00 |
| Butyl Acetate | 15.00 | 15.00 |
| Ethyl Alcohol | 5.00 | 5.00 |
| Toluene | 35.00 | 35.00 |
| Total | 100.00 | 100.00 |

Properties, such as application degree, concealment, color, and matte properties, of the lipsticks, eye shadows and nail polishes prepared according to compositions listed in Tables 5 to 7 are shown in Table 8.

In order to evaluate application degree, concealment, color and matte properties of each product, sensory evaluation (score 0 to score 100), such as opinions after use of the products as cosmetics, and the like, was performed by 40 women aged 20 to 40, scores were provided and rated according to average values, as follows:

X (score below 60): Bad
Δ (score 60 to score 69): Medium
o (score 70 to score 79): Relatively Good
◎ (score 80 to score 89): Excellent
● (score 90 to score 100): Extremely Excellent

TABLE 8

| Type of cosmetics | Pigment | Application degree | Concealment | Color | Matte properties |
|---|---|---|---|---|---|
| Lipstick | Example 2 | ● | ● | ◎ | ● |
|  | Comparative pigment | ○ | ◎ | ◎ | ○ |
| Eye shadow | Example 2 | ● | ● | ◎ | ◎ |
|  | Comparative pigment | ○ | ○ | ◎ | ○ |
| Nail polish | Example 2 | ◎ | ● | ◎ | ● |
|  | Comparative pigment | ○ | ◎ | ◎ | ○ |

Referring to Table 8, when the pigment prepared in Example 2 was used as a cosmetic pigment, it was confirmed that the cosmetics exhibited excellent properties in terms of application degree, concealment, transparency and color. This means that the silver-coated pigment according to the invention enables high-gloss color expression while maintaining functions equal or superior to typical cosmetic pigments.

Although the present invention has been described with reference to some embodiments, it should be understood that various modifications, changes, alterations, and equivalent embodiments can be made by those skilled in the art without departing from the spirit and scope of the invention. Therefore, the scope of the invention should be limited only by the accompanying claims and equivalents thereof.

The invention claimed is:

1. A method for preparing a silver (Ag)-coated pigment, comprising:
   forming a tin compound pre-treatment layer on a surface of a matrix formed of at least one material of glass flakes, mica, titania-coated glass flakes, titania-coated mica, iron oxide coated mica, iron oxide coated glass flakes, plate-shaped iron oxide, plate-shaped alumina, and plate-shaped silica; and
   forming a silver coating layer on the tin compound pre-treatment layer through refluxing and electroless plating utilizing a dilute silver nitrate solution, aqueous ammonia, a citric acid solution, and a dilute potassium hydroxide solution.

2. The method according to claim 1, wherein the tin compound pre-treatment layer is formed in a weight ratio from 1 part by weight to 10 parts by weight based on 100 parts by weight of the matrix, and the silver coating layer is formed in a weight ratio from 10 parts by weight to 35 parts by weight based on 100 parts by weight of the matrix.

3. The method according to claim 2, wherein the silver coating layer has a bacteria removal rate of 99.9% or more according to antibacterial activity testing, and has a electromagnetic wave shielding rate of 10 dB or more.

4. A method for preparing a silver (Ag)-coated pigment comprising:
  (a) preparing a slurry by mixing a matrix with a hydrochloric acid solution;
  (b) removing impurities from a surface of the matrix by refluxing the slurry;
  (c) forming a $SnCl_2$ pre-treatment layer on the surface of the matrix by adding $SnCl_2.2H_2O$ to the slurry of (b) and refluxing the slurry;
  (d) forming pigment powder coated with the $SnCl_2$ pre-treatment layer through dehydration and water-washing of the slurry;
  (e) forming a dilute silver nitrate solution by mixing silver nitrate, pure water, aqueous ammonia and sodium citrate, and forming a suspension by mixing the pigment powder coated with the $SnCl_2$ pre-treatment layer with the dilute silver nitrate solution;
  (f) mixing the suspension with a dilute glucose solution and refluxing the mixture;
  (g) mixing the suspension of (f) with a dilute potassium hydroxide (KOH) solution and additionally refluxing the resulting suspension;
  (h) adding a citric acid solution to the suspension of (g), and forming a silver (Ag) coating layer on the pre-treatment layer by refluxing and electroless plating the suspension; and
  (i) performing dehydration and washing with water of the suspension of (h), and drying the suspension.

5. The method according to claim 4, wherein, in (a), the hydrochloric acid solution comprises 1 wt % to 10 wt % of hydrochloric acid, and the slurry has a solid content of 10 wt % to 20 wt %.

6. The method according to claim 4, wherein in (b) and (c), refluxing is performed for 1 hour to 3 hours.

7. The method according to claim 4, wherein in (e), the dilute silver nitrate solution comprises 10 parts by weight to 70 parts by weight of the silver nitrate based on 100 parts by weight of the matrix, the aqueous ammonia is present in an amount of 50 parts by weight to 150 parts by weight based on 100 parts by weight of the silver nitrate, and the sodium citrate is present in an amount of 15 parts by weight to 100 parts by weight based on 100 parts by weight of the silver nitrate.

8. The method according to claim 4, wherein the dilute glucose solution of (f) comprises 100 parts by weight to 200 parts by weight of glucose based on 100 parts by weight of the silver nitrate.

9. The method according to claim 4, wherein the dilute potassium hydroxide (KOH) solution comprises 100 parts by weight to 200 parts by weight of potassium hydroxide based on 100 parts by weight of the silver nitrate, and is added over 30 minutes to 3 hours using a metering pump.

10. The method according to claim 4, wherein in (h), the added citric acid solution is added in an amount of 50 parts by weight to 200 parts by weight based on 100 parts by weight of the silver nitrate.

11. The method according to claim 4, wherein in (i), drying is performed at 30° C. to 100° C.

* * * * *